United States Patent
Hanson

Patent Number: 5,961,330
Date of Patent: Oct. 5, 1999

[54] VIAL FOR DENTAL IMPLANT DELIVERY SYSTEM

[75] Inventor: Steven E. Hanson, San Diego, Calif.

[73] Assignee: Sulzer Calcitek Inc., Carlsbad, Calif.

[21] Appl. No.: 09/058,017

[22] Filed: Apr. 9, 1998

[51] Int. Cl.⁶ .............................................. A61C 8/00
[52] U.S. Cl. .............................................. 433/173; 433/77
[58] Field of Search .................... 433/77, 172, 173, 433/174, 175; 206/63.5, 368

[56] References Cited

U.S. PATENT DOCUMENTS

| | | | |
|---|---|---|---|
| Re. 8,112 | 3/1878 | Frazier . | |
| D. 263,878 | 4/1982 | Edwardson | D24/16 |
| D. 264,125 | 4/1982 | Biggs | D24/10 |
| D. 265,246 | 6/1982 | Jermyn | D24/33 |
| D. 268,615 | 4/1983 | Biggs | D24/10 |
| D. 273,984 | 5/1984 | Vlock | D24/10 |
| D. 281,904 | 12/1985 | Linkow et al. | D24/33 |
| D. 282,580 | 2/1986 | Linkow et al. | D24/33 |
| D. 290,506 | 6/1987 | Weissman | D24/10 |
| D. 290,507 | 6/1987 | Weissman | D24/10 |
| D. 290,508 | 6/1987 | Weissman | D24/10 |
| D. 294,295 | 2/1988 | Branemark | D24/33 |
| D. 296,362 | 6/1988 | Branemark | D24/33 |
| D. 314,821 | 2/1991 | Miller | D24/10 |
| D. 314,822 | 2/1991 | Miller | D24/10 |
| D. 317,200 | 5/1991 | Jorneus | D24/156 |
| D. 319,500 | 8/1991 | Soderberg | D24/156 |
| D. 321,560 | 11/1991 | Miller | D24/156 |
| D. 324,731 | 3/1992 | Sullivan | D24/156 |
| D. 325,085 | 3/1992 | Branemark et al. | D24/156 |
| D. 330,767 | 11/1992 | Jorneus | 24/10 |
| D. 331,282 | 11/1992 | Kallus | D24/156 |
| D. 336,683 | 6/1993 | Inoue et al. | D24/156 |
| D. 338,959 | 8/1993 | Loof et al. | D24/156 |
| D. 342,314 | 12/1993 | Miller | D24/156 |
| D. 351,904 | 10/1994 | Maze | D24/121 |
| D. 353,674 | 12/1994 | Jorneus | D24/156 |
| D. 355,487 | 2/1995 | Broberg | D24/156 |
| D. 355,972 | 2/1995 | Broberg et al. | D24/156 |
| D. 356,868 | 3/1995 | Broberg et al. | D24/156 |
| D. 356,869 | 3/1995 | Holmen et al. | D24/156 |
| D. 358,212 | 5/1995 | Sullivan | D24/156 |
| D. 366,115 | 1/1996 | Sulivan | D24/156 |
| D. 370,978 | 6/1996 | Broberg et al. | D24/156 |
| D. 374,079 | 9/1996 | Broberg | D24/156 |
| D. 374,080 | 9/1996 | Broberg | D24/156 |
| 394,376 | 12/1888 | Kelton . | |
| 853,984 | 5/1907 | Lauderdale . | |
| 1,257,947 | 2/1918 | Sternberg . | |
| 1,812,008 | 6/1931 | Lace . | |
| 3,378,925 | 4/1968 | Faller | 32/71 |
| 3,579,306 | 5/1971 | Crane | 23/253 |
| 3,703,977 | 11/1972 | Plsarek | 221/213 |
| 3,874,081 | 4/1975 | Franklin et al. | 32/15 |
| 3,890,204 | 6/1975 | Avery | 195/139 |
| 3,990,438 | 11/1976 | Pritchard | 128/92 |
| 4,027,392 | 6/1977 | Sawyer et al. | 32/10 |
| 4,177,562 | 12/1979 | Miller et al. | 433/174 |
| 4,180,192 | 12/1979 | Breslau | 224/235 |
| 4,189,834 | 2/1980 | Smith | 433/225 |
| 4,220,712 | 9/1980 | Staffolani | 433/173 |
| 4,234,309 | 11/1980 | Sellers | 433/225 |
| 4,253,829 | 3/1981 | Adelberger | 433/40 |
| 4,259,072 | 3/1981 | Hirabayashi et al. | 433/173 |
| 4,364,473 | 12/1982 | Bogaert | 206/63.5 |
| 4,444,310 | 4/1984 | Odell | 206/366 |
| 4,445,611 | 5/1984 | Shofu | 206/369 |
| 4,451,237 | 5/1984 | Fihol | 433/225 |
| 4,553,942 | 11/1985 | Sutter | 433/225 |

(List continued on next page.)

FOREIGN PATENT DOCUMENTS

| | | |
|---|---|---|
| 0312698 | of 0000 | European Pat. Off. . |
| 2421990 A1 | 11/1975 | Germany . |
| 1727808 | 4/1992 | U.S.S.R. . |

*Primary Examiner*—John J. Wilson
*Assistant Examiner*—Patrick A. Hilsmier
*Attorney, Agent, or Firm*—Philip S. Lyren

[57] ABSTRACT

A dental implant delivery system comprising a vial having two cavities. One cavity in the body of the vial houses an implant and a driver mount, and the other cavity in the lid of the vial houses a healing screw.

16 Claims, 2 Drawing Sheets

U.S. PATENT DOCUMENTS

| | | | |
|---|---|---|---|
| 4,579,531 | 4/1986 | Hinks | 433/225 |
| 4,615,462 | 10/1986 | Sacherer et al. | 220/339 |
| 4,616,999 | 10/1986 | Weissman | 433/225 |
| 4,671,410 | 6/1987 | Hansson et al. | 206/438 |
| 4,712,681 | 12/1987 | Branemark et al. | 206/438 |
| 4,713,003 | 12/1987 | Symington et al. | 433/173 |
| 4,717,018 | 1/1988 | Sacherer | 206/305 |
| 4,722,733 | 2/1988 | Howson | 604/411 |
| 4,758,161 | 7/1988 | Niznick | 433/173 |
| 4,763,788 | 8/1988 | Jorneus et al. | 206/438 |
| 4,850,870 | 7/1989 | Lazzara et al. | 433/174 |
| 4,850,874 | 7/1989 | Weissman | 433/225 |
| 4,856,648 | 8/1989 | Krueger | 206/63.5 |
| 4,856,994 | 8/1989 | Lazzara et al. | 433/173 |
| 4,915,629 | 4/1990 | Sellers | 433/173 |
| 4,927,363 | 5/1990 | Schneider | 433/173 |
| 4,942,991 | 7/1990 | Lyons | 224/196 |
| 4,955,811 | 9/1990 | Lazzara et al. | 433/173 |
| 4,964,801 | 10/1990 | Kawahara et al. | 433/173 |
| 4,976,617 | 12/1990 | Carchidi | 433/141 |
| 4,978,007 | 12/1990 | Jacobs et al. | 206/469 |
| 5,018,970 | 5/1991 | Stordahl | 433/75 |
| 5,026,285 | 6/1991 | Durr et al. | 433/173 |
| 5,030,095 | 7/1991 | Niznick | 433/173 |
| 5,030,096 | 7/1991 | Hurson et al. | 433/173 |
| 5,035,619 | 7/1991 | Daftary | 433/173 |
| 5,049,073 | 9/1991 | Lauks | 433/173 |
| 5,049,074 | 9/1991 | Otani et al. | 433/173 |
| 5,062,800 | 11/1991 | Niznick | 433/229 |
| 5,069,336 | 12/1991 | Mauthe | 206/219 |
| 5,073,111 | 12/1991 | Daftary | 433/173 |
| 5,078,607 | 1/1992 | Niznick | 433/174 |
| 5,085,586 | 2/1992 | Johnson | 433/224 |
| 5,087,201 | 2/1992 | Mondani et al. | 433/174 |
| 5,100,323 | 3/1992 | Friedman et al. | 433/173 |
| 5,106,300 | 4/1992 | Voitik | 433/173 |
| 5,117,976 | 6/1992 | Whitt | 206/333 |
| 5,125,840 | 6/1992 | Durr et al. | 433/173 |
| 5,145,372 | 9/1992 | Daftary et al. | 433/173 |
| 5,167,664 | 12/1992 | Hodorek | 606/73 |
| 5,180,303 | 1/1993 | Hornburg et al. | 433/173 |
| 5,197,881 | 3/1993 | Chalifoux | 433/173 |
| 5,209,659 | 5/1993 | Friedman et al. | 433/173 |
| 5,236,361 | 8/1993 | Mays | 433/221 |
| 5,246,369 | 9/1993 | Poulmaire | 433/173 |
| 5,270,011 | 12/1993 | Altherr | 422/102 |
| 5,281,140 | 1/1994 | Niznick | 433/172 |
| 5,282,746 | 2/1994 | Sellers et al. | 433/172 |
| 5,297,963 | 3/1994 | Daftary | 433/172 |
| 5,312,254 | 5/1994 | Rosenlicht | 433/173 |
| 5,344,457 | 9/1994 | Pilliar et al. | 623/16 |
| 5,350,297 | 9/1994 | Cohen | 433/76 |
| 5,362,235 | 11/1994 | Daftary | 433/172 |
| 5,366,374 | 11/1994 | Vlassis | 433/165 |
| 5,368,160 | 11/1994 | Leuschen et al. | 206/339 |
| 5,409,377 | 4/1995 | Mays | 433/220 |
| 5,415,545 | 5/1995 | Shaw | 433/173 |
| 5,431,567 | 7/1995 | Daftary | 433/172 |
| 5,484,285 | 1/1996 | Morgan et al. | 433/173 |
| 5,501,706 | 3/1996 | Arenberg | 623/16 |
| 5,538,426 | 7/1996 | Harding et al. | 433/172 |
| 5,538,428 | 7/1996 | Staubli | 433/173 |
| 5,558,230 | 9/1996 | Fischer et al. | 226/570 |
| 5,564,924 | 10/1996 | Kwan | 433/173 |
| 5,582,299 | 12/1996 | Lazzara et al. | 206/63.5 |
| 5,584,694 | 12/1996 | Forsmalm et al. | 433/172 |
| 5,622,500 | 4/1997 | Niznick | 433/173 |
| 5,636,989 | 6/1997 | Somborac | 433/173 |
| 5,636,991 | 6/1997 | Mays | 433/220 |
| 5,667,094 | 9/1997 | Rapchak et al. | 220/339 |
| 5,685,715 | 11/1997 | Beaty et al. | 433/173 |
| 5,702,695 | 12/1997 | Clokie | 424/78.08 |
| 5,711,468 | 1/1998 | Shoemaker | 224/251 |
| 5,755,575 | 5/1998 | Biggs | 433/173 |

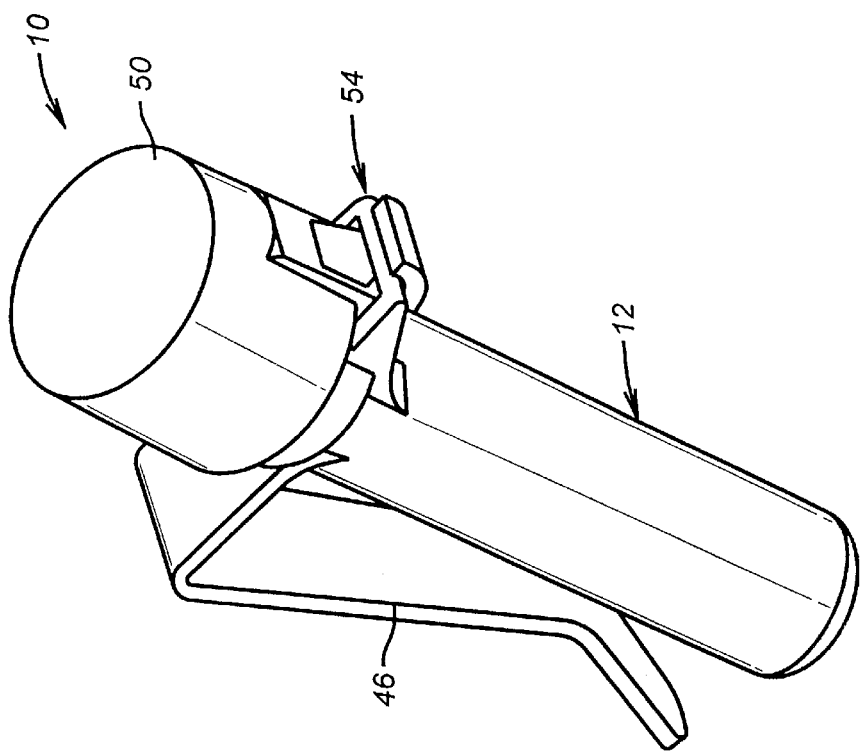
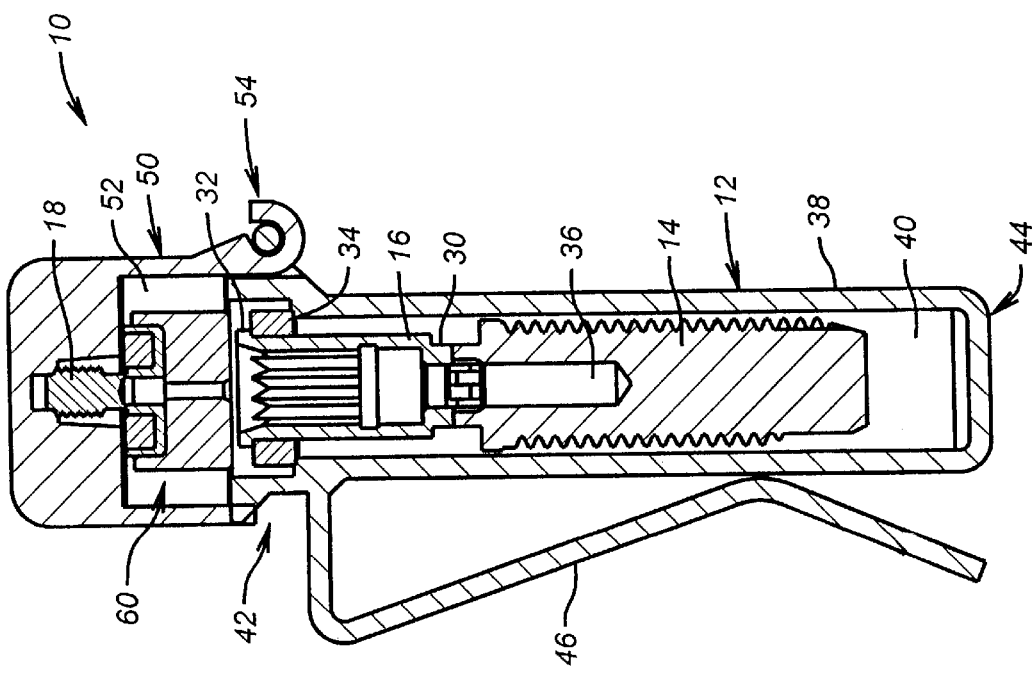

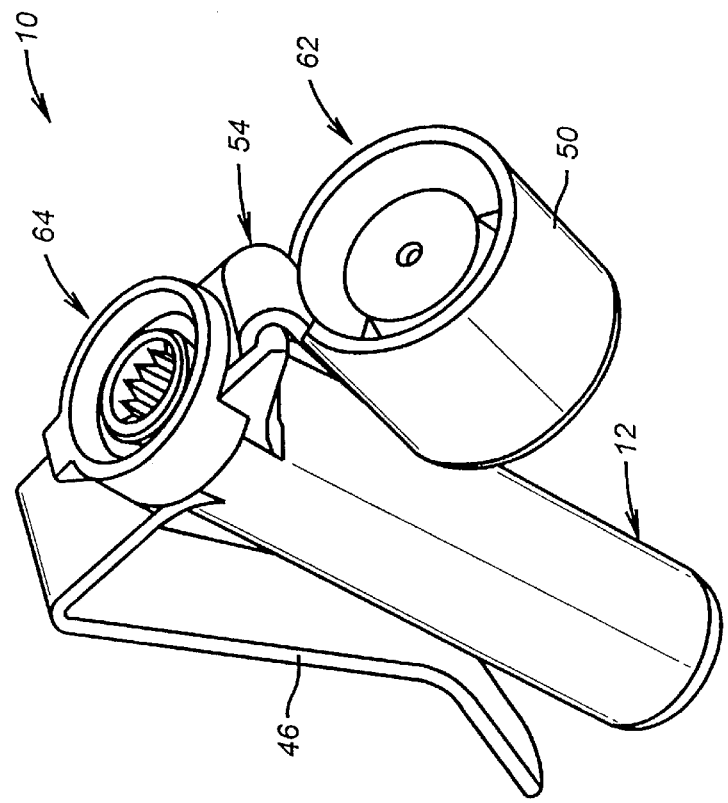
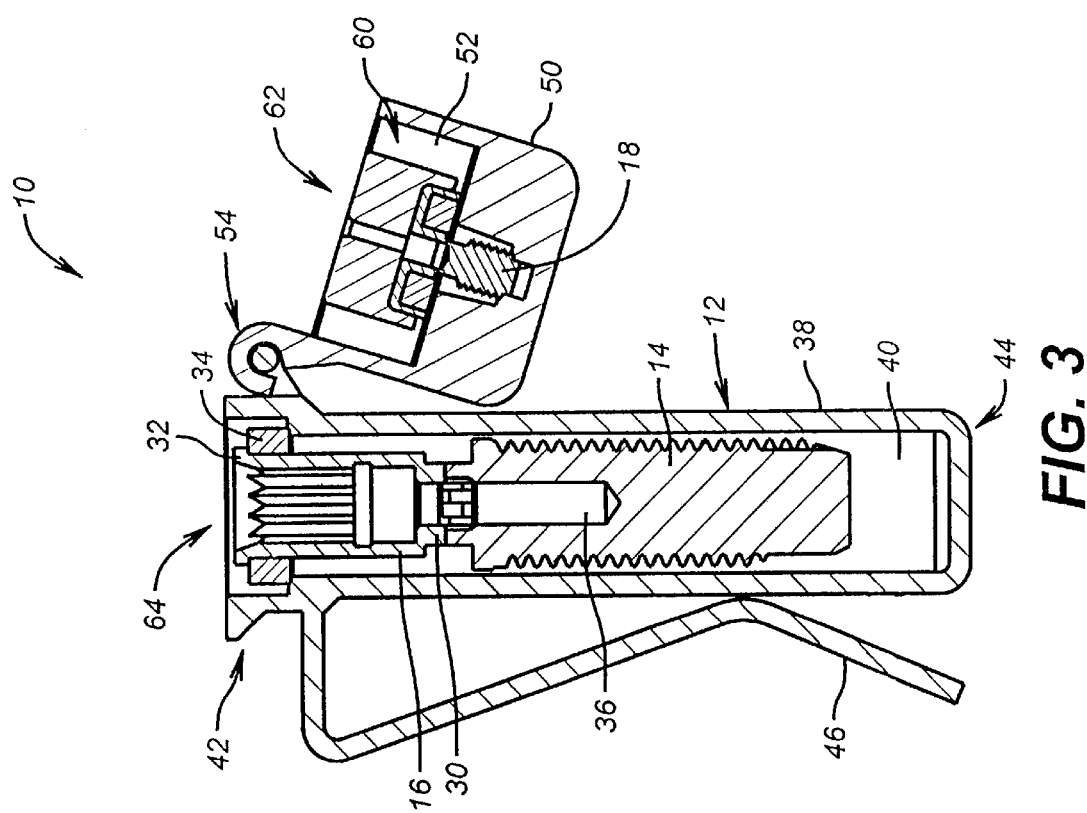

VIAL FOR DENTAL IMPLANT DELIVERY SYSTEM

BACKGROUND OF THE INVENTION

Threaded dental implants are typically packaged and shipped in a package known as an implant delivery system. The delivery system typically includes a vial containing the threaded implant, a driver mount, and a healing screw. The vial is then shipped in sterile packaging until the implant is needed during a surgical implantation procedure.

The vial usually has an elongated cylindrical configuration forming an inner cavity to hold the implant, driver mount, or healing screw. These three components may be transported in one or two vials. Typically, a lid fits on top of the vial to seal and retain the components in the cavity.

In order to install the implant during a surgical procedure, an implant site is prepared using conventional surgical procedures. Typically, an incision is made along the gingival tissue at the implant site, and a cylindrical bore is drilled into the bone. Once the site is fully prepared, the lid is removed from the vial, and the implant, driver mount, and healing screw are all removed. The healing screw is disconnected from the driver mount, and a driving tool, such as a motorized dental hand-piece, is connected to the free end of the driver mount using an adapter. The implant and driver mount are moved to the implant site, and the end of the implant is driven into the bore. The driver mount is then removed from the implant, and the healing screw is placed on the coronal end of the implant. The gingival tissue is then sutured and the implant remains within the bone for several months as osseointegration and healing occur. During a second surgical procedure, the implant is re-exposed, the healing screw is removed, and a dental prosthesis is affixed to the implant.

One important disadvantage associated with prior dental delivery systems using a single vial is that the healing screw is connected to the implant or driver mount. As a consequence, direct access to the implant or driver mount is not possible without first moving or removing the healing screw. Moving the healing screw adds unwanted time and surgical steps to the implantation procedure.

Some prior delivery systems use two separate vials or large, bulky containers having multiple cavities to hold the implant, driver mount, and healing screw. For example, some delivery systems store the healing screw in one container and the implant and driver mount in another container. Still other delivery systems have two separate cavities, for example a container having two side-by-side cavities. One cavity holds the implant and driver mount while the other cavity holds the healing screw. None of these systems use a single vial to hold the implant, driver mount, and healing screw. Instead, these.

It would be advantageous to employ a dental implant delivery system that utilizes a single vial that houses the implant, driver mount, and healing screw and that gives direct and simultaneous access to the implant and driver mount and healing screw. Such a delivery system would more effectively hold these components to reduce the time and number of steps during a dental implantation procedure. A surgical procedure requiring fewer steps ultimately would be less traumatic to the patient, more expeditiously performed, and less burdensome on the surgeon, to name a few examples.

Further yet, such a delivery system would minimize the amount of handling of the system components.

The present invention solves the problems discussed above with prior dental delivery systems and provides further advantages.

SUMMARY OF THE INVENTION

The present invention is directed toward a vial for a dental implant delivery system. The vial provides direct and simultaneous access to both the healing screw and the implant once a lid on top of the vial is open. When the lid is open, the driver mount and implant may be removed with a single step and the healing screw may be removed with a single step.

The vial has an elongated cylindrical configuration with a body portion forming a first interior cavity and a lid forming a second interior cavity. This first cavity houses the implant and the driver mount, and this second cavity houses the healing screw. The lid may be moved between a closed and open position. In the closed position, the lid covers the top of the body portion and seals the two cavities together. In the open position, the lid moves to a position adjacent the body portion and enables direct access to both cavities.

The invention, accordingly, comprises the apparatus and method possessing the construction, combination of elements, and arrangement of parts that are exemplified in the following detailed description. For a fuller understanding of the nature and objects of the invention, reference should be made to the following detailed description taken in connection with the accompanying drawings.

BRIEF DESCRIPTION OF THE DRAWINGS

FIG. 1 is a cross sectional view of a closed vial of a dental implant delivery system;

FIG. 2 is a perspective view of the closed vial of FIG. 1.

FIG. 3 is a cross sectional view of an open vial of the dental implant delivery system; and FIG. 4 is a perspective view of the open vial of FIG. 3.

DETAILED DESCRIPTION OF THE PREFERRED EMBODIMENTS

FIGS. 1–4 depict a dental implant delivery system 10 comprising a vial 12, a threaded implant 14, a driver mount 16, and a healing screw 18.

Implant 14 may be any one of various implants known to those skilled in the art, such as a TWIST™ implant manufactured by Sulzer Calcitek Inc. of Carlsbad, Calif.

Driver mount 16 has a generally elongated cylindrical configuration having two ends 30 and 32, respectively. End 30 is configured to abut against the coronal end of the implant and includes a plurality of splines that project downwardly to engage corresponding splines of the implant. The engagement between these splines provides an anti-rotational connection between the driver mount and implant. This anti-rotational connection may be established with other configurations known to those skilled in the art, such as a mating hexagonal projection and recess.

The other end 32 of the driver mount includes a flange 34. This flange abuts against a shoulder on the interior of the vial and suspends the implant and driver mount. A retaining screw 36 connects the driver mount to the implant. The screw passes axially through end 32 and into a channel within the driver mount and engages threads located in a cavity in the implant.

Vial 12 has an elongated cylindrical body 38 forming an interior hollow cavity 40 housing the implant and driver mount. Cavity 40 extends from a top portion 42 toward a bottom portion 44.

Vial 12 further includes a clip 46 that extends along one side of the body. The clip is formed from a flexible arm that is able to securely attach and support the vial. The clip, for example, may attach the vial to the periphery of a dental surgical tray (not shown).

The vial also includes a lid 50 forming an interior cavity 52, separate from cavity 40 in body 38. The lid is connected to top portion 42 with a hinge assembly 54. The hinge assembly enables the lid to move from a closed position (shown in FIGS. 1 and 2) to an open position (shown in FIGS. 3 and 4). Preferably, the lid remains attached to the body of vial in the open position, as shown in FIGS. 3 and 4. As such, no refuse or secondary waste is generated when the lid is opened.

The lid may be connected to the body of the vial with various different attachments known to those skilled in the art. For example, a flexible arm (not shown) may connect the lid to the body of the vial. The arm could function as a spring and automatically bias the lid away from the body immediately after the lid is open.

Looking to FIGS. 1 and 2, in the closed position, lid 50 fits onto top portion 42 to enclose cavities 40 and 52. The connection between the lid and the top portion is sufficient to cover these cavities. In alternative embodiments, the lid may seal these cavities and maintain them in a sterile environment.

Further, in the closed position, healing screw 18 is directly above the implant and driver mount. In this position, the screw, implant, and driver mount are housed within a single cavity comprising cavity 40 and cavity 52. A separate vial or container for the healing screw is thus not needed.

As seen in the FIGS. 1 and 3, healing screw 18 connects to a delivery cap 60. This cap holds the healing screw in lid. When the lid is in the closed position, as seen in FIG. 1, the delivery cap abuts against end 32 of the driver mount to stabilize the implant, driver mount, and healing screw. Alternatively, a small gap (not shown) may be provided between the delivery cap and end 32. In both embodiments, the spacial relationship between the delivery cap and the driver mount minimizes movement of these components during shipping and handling of the vial.

One important advantage with the present invention is that a single vial houses both the implant and the healing screw, and once the vial is open, simultaneous access to both the implant and the screw is possible.

As shown in FIGS. 3 and 4, in the open position, the lid is adjacent top portion 42 of the body of the vial. One opening 62 gives access to the healing screw, and a second opening 64 gives access to the implant. Thus, a single action of opening the lid provides immediate access to both the healing screw and the implant. Openings 62 and 64 are adjacent each in the open position to facilitate access to each cavity. Preferably, these openings reside in a common plane or closely residing planes. The separate cavities also expedite the implantation procedure.

Use of the implant delivery system is now discussed in more detail with reference to FIGS. 1–4. During storage and transportation of the implant delivery system, the implant, driver mount, and healing screw remain in a protected environment in the vial. During a dental implantation procedure, lid 50 is opened. The implant is exposed in one cavity, and the healing screw is exposed in another cavity. A driving tool, such as a motorized driver or ratchet wrench, and an adapter are then affixed to end 32, and the implant and driver mount are removed from the vial. The distal end of the implant is then positioned into the osteotomy site. The driving tool then imparts a driving force to the driver mount that, in turn, imparts this same force to the implant.

Once the implant is fully seated and positioned, the driving tool is removed from end 32. A separate removal tool is then used to loosen and remove retaining screw 36. The driver mount is removed from the implant. The noted driving tool is then used to remove the healing screw from cavity 52. Using the same driving tool to remove and drive both the driver mount and healing screw reduces the overall number of surgical steps in the implantation procedure. This driving tool is affixed to the end of delivery cap 60, and the cap and screw are simultaneously removed from cavity 52. The cap and screw are then placed over the coronal end of the implant until the screw fits within the implant. Thereafter, the cap is disengaged from the screw, and the screw is left to cover the implant. Conventional procedures are then used to finish the surgical procedure and thereafter connect a prosthesis to the implant.

In alternate method, once the implant is fully seated and positioned, the driving tool is removed from end 32. A separate removal tool is then used to loosen and remove retaining screw 36. The driver mount is removed from the implant. The separate removal tool is then used to remove the healing screw from cavity 52. Using the same removal tool to remove and drive both the driver mount and healing screw reduces the overall number of surgical steps in the implantation procedure. This removal tool is affixed to the end of delivery cap 60, and the cap and screw are simultaneously removed from cavity 52. The cap and screw are then placed over the coronal end of the implant until the screw fits within the implant. Thereafter, the cap is disengaged from the screw, and the screw is left to cover the implant. Conventional procedures are then used to finish the surgical procedure and thereafter connect a prosthesis to the implant.

Since certain changes may be made in the above-described apparatus and method without departing from the scope of the invention herein involved, all matter contained in the description or shown in the accompanying drawings shall be interpreted as illustrative and not in a limiting sense.

The invention claimed is:

1. A dental implant delivery system, comprising:
    a vial including a body having an elongated cylindrical configuration forming a first interior cavity, a lid having a cylindrical configuration forming a second interior cavity, and a hinge assembly connecting said lid to said body;
    a dental implant having a cylindrical configuration and external threads;
    a driver mount connected to a coronal end of said implant, with said implant and said driver mount disposed in said first cavity; and
    a healing screw disposed in said second cavity.

2. The delivery system of claim 1 in which:
    said lid is moveable between an open position and a closed position;
    in said closed position, said lid fits on top of said body with said healing screw disposed directly above said implant and said driver mount; and
    in said open position, said lid is removed from said top of said body and disposed next to said body while remaining attached to said hinge assembly.

3. The delivery system of claim 2 in which said lid remains connected to said body in both said open and closed positions.

4. The delivery system of claim 1 in which:
    a first opening leads to said first cavity;
    a second opening leads to said second cavity;

said lid is moveable between an open position and a closed position;

in said closed position, said lid abuts said body to enclose said first and second cavities; and in said open position, said lid is adjacent said body such that said first opening allows direct access to said first cavity and said second opening allows direct access to said second cavity.

5. The delivery system of claim 4 in which said first opening and said second opening are substantially in a common plane when in said open position.

6. The delivery system of claim 5 in which said lid is connected to said body in said open position.

7. The delivery system of claim 1 in which:

said delivery system further comprises a delivery cap in said second cavity and connected to said healing screw;

said lid is moveable between an open and closed position;

in said closed position, said lid fits on top of said body such that said delivery cap abuts against one end of said driver mount; and in said open position, said lid is off the top of said body to provide access to said first and second cavities.

8. The delivery system of claim 1 in which: said lid is moveable between an open position and a closed position;

in said closed position, said lid forms an extension of said body with said first and second cavities forming a single cavity; and in said open position, said first and second cavities are disconnected and separate to allow simultaneous access to said implant and driver mount in said first cavity and to said healing screw in said second cavity.

9. A vial for a dental implant delivery system, comprising:

a body having an elongated cylindrical configuration forming a first opening leading to a first cylindrical cavity housing a dental implant;

a lid having a cylindrical configuration forming a second opening leading to a second cylindrical cavity housing a dental healing screw;

a hinge assembly connecting said lid to said body such that said lid is moveable between a closed position and an open position;

said lid fitting on top of said body in said closed position to enclose said first and second cavities; and said lid moving adjacent said body in said open position to provide simultaneous access to said first cavity through said first opening and to said second cavity through said second opening.

10. The vial of claim 9 in which said lid remains connected to said body in said closed and open positions.

11. The vial of claim 9 in which said first and second openings are adjacent one another and substantially in a common plane while in said open position.

12. The vial of claim 9 in which said first cavity extends substantially along the length of said body.

13. The vial of claim 9 in which:

said first and second cavities are connected in said closed position to form a third cavity that comprises a combination of said first and second cavities; and said first and second cavities are separated in said open position to form two distinct cavities.

14. The vial of claim 9 in which said first and second cavities extend substantially the entire length of said vial in said closed position.

15. A method for implanting a dental implant, comprising the steps:

providing a dental implant delivery system including a vial having a body with a first cavity and a lid connected to said body and with a second cavity, a dental implant disposed within said first cavity, a driver mount connected to said implant, and a healing screw disposed in said second cavity;

drilling a bore in a jawbone of a patient to be implanted with said dental implant;

moving said lid from a closed position on top of said body to an open position next to a top portion of said body to provide direct access to both said first and second cavities;

connecting a driving tool to said drive mount in said first cavity;

removing said implant and driver mount from said first cavity;

positioning a distal end of said implant in said bore;

driving said implant into said bore;

removing said driving tool from said driver mount;

removing said driver mount from said implant;

connecting said driving tool to said healing screw in said second cavity;

removing said healing screw from said second cavity;

connecting said healing screw to a coronal end of said implant; and removing said driving tool from said healing screw.

16. The method of claim 15 further comprising the steps of: providing said implant delivery system with a delivery cap located in said second cavity and connected to said healing screw and; removing said delivery cap from said healing screw after said step of connecting said healing screw to a coronal end of said implant.

* * * * *